(12) United States Patent
Kulkarni et al.

(10) Patent No.: US 6,239,317 B1
(45) Date of Patent: May 29, 2001

(54) PROCESS FOR THE PRODUCTION OF HALOGENO-O-HYDROXYDIPHENYL COMPOUNDS

(75) Inventors: Surendra Umesh Kulkarni; Vadiraj Subbanna Ekkundi; Pradeep Jeevaji Nadkarni; Chandrasekhar Dayal Mudaliar; Kishore Ramachandra Nivalkar, all of Mumbai (IN)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/019,378

(22) Filed: Feb. 5, 1998

(30) Foreign Application Priority Data

Jun. 25, 1997 (DE) .................................................. 97810408

(51) Int. Cl.$^7$ .................................................. C07C 37/00
(52) U.S. Cl. ..................... 568/803; 568/626; 568/630; 568/631; 568/655; 568/656; 568/804; 560/62
(58) Field of Search ..................... 568/626, 630, 568/631, 655, 656, 803, 804; 560/62

(56) References Cited

U.S. PATENT DOCUMENTS

| 3,629,477 | * | 12/1971 | Model et al. | 424/340 |
| 4,950,809 | | 8/1990 | Gubelmann | 568/741 |

FOREIGN PATENT DOCUMENTS

| 322983 | * | 5/1989 | (EP) | C07C/47/575 |
| 0857711 | * | 12/1998 | (EP) | C07C/43/295 |

OTHER PUBLICATIONS

Atkinson et al, vol. 26, No. 10, (1983), pp. 1353–1360.
"The Merck Index, 12$^{th}$ Ed." (1996), p. 1646, Compound No. 9790.

Yeager et al., "An Umpoled Synthon Approach to the Synthesis of 2–Aryloxyphenols", Synthesis (1), pp. 28–30 (1995).
Watson et al., "Non Catalytic Chlorination of Diphenyl Ether", Journal of Organic Chemistry, 44(7), pp. 1155–1158 (1979).
Atkinson et al., Journal of Medicinal Chemistry, vol. 26(10), pp. 1353–1360, 1983.*

* cited by examiner

Primary Examiner—Gary Geist
Assistant Examiner—Howard Owens
(74) Attorney, Agent, or Firm—Kevin T. Mansfield

(57) ABSTRACT

There is described a four step process for the production of halogeno-o-hydroxydiphenyl compounds having the formula

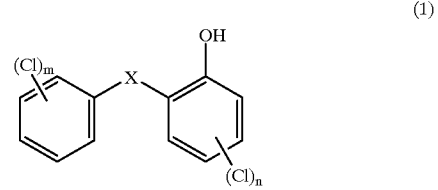

(1)

in which X is —O— or —CH$_2$—;
m is 1 to 3; and
n is 1 or 2;

wherein in the first step, a diphenyl compound is chlorinated; in a second step the chlorinated compound is acylated in a Friedel-Crafts reaction and optionally again chlorinated after the acylation; in a third step the acyl compound is oxidised; and in a fourth step the oxidized compound is hydrolyzed.

The compounds of formula (1) are useful for the protection of organic materials against microorganisms.

14 Claims, No Drawings

PROCESS FOR THE PRODUCTION OF HALOGENO-O-HYDROXYDIPHENYL COMPOUNDS

The present invention relates to the production of halogeno-o-hydroxydiphenyl compounds having the formula:

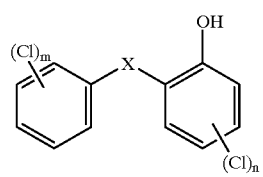

(1)

in which

X is —O— or —CH$_2$—;

m is 1 to 3; and n is 1 or 2;

as well as to the use of these compounds for the protection of organic materials against microorganisms or in e.g. cosmetic compositions.

The production of halogeno-o-hydroxydiphenyl compounds, especially of 2-hydroxy-2',4,4'-trichlorodiphenylether (Triclosan; compound of formula (3) below), is usually effected by diazotisation and subsequent hydrolysis of 2-amino-2',4,4'-trichlorodiphenylether (TADE; compound of formula (2) below):

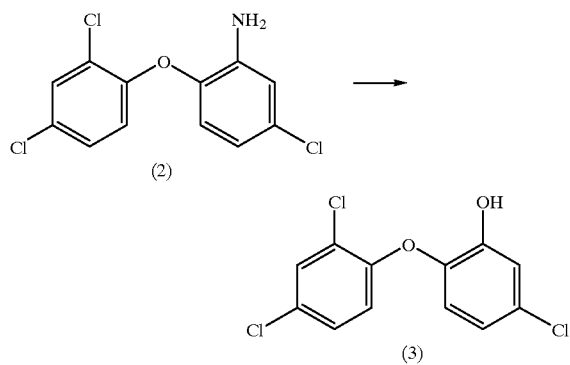

The yields obtained by this production method are unsatisfactory, however, since various chemically competing reactions can occur.

The object of the present invention, therefore, is the provision of an economic process for the production of halogeno-o-hydroxydiphenyl compounds in which undesired side-reactions are suppressed.

According to the present invention, there is provided a four-step process for the production of halogeno-o-hydroxydiphenyl compounds in which, in the first step, a diphenyl compound is chlorinated; in a second step the chlorinated compound is acylated in a Friedel-Crafts reaction and optionally again chlorinated after the acylation; in a third step the acyl compound is oxidized; and in a fourth step the oxidized compound is hydrolyzed; according to the following reaction scheme:

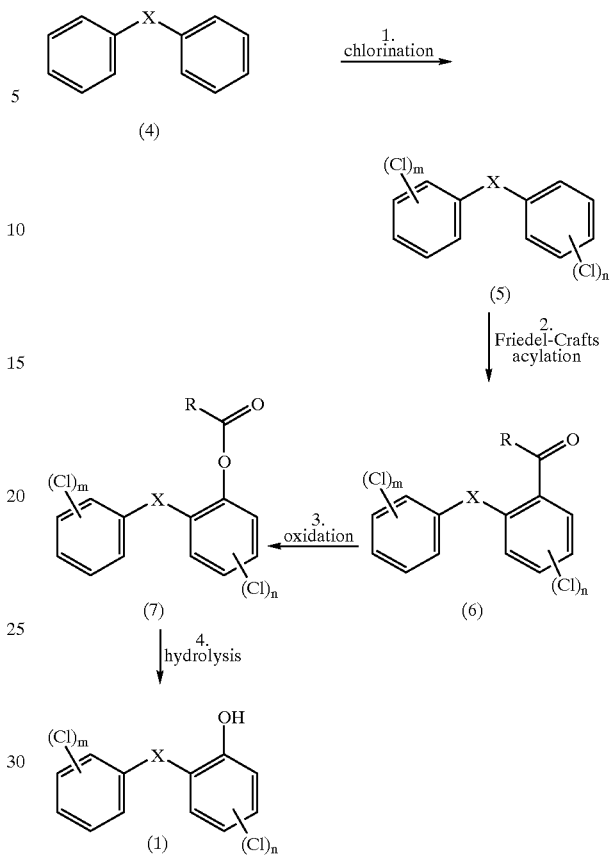

In the above scheme:

R is unsubstituted C$_1$–C$_8$alkyl or C$_1$–C$_8$alkyl substituted by 1 to 3 halogen atoms or hydroxy; or unsubstituted C$_6$–C$_{12}$aryl or C$_6$–C$_{12}$aryl substituted by 1 to 3 halogen atoms, C$_1$–C$_5$alkyl or C$_1$–C$_8$alkoxy or combinations thereof;

X is —O— or —CH$_2$—;

m is 1 to 3; and n is 1 or 2.

C$_1$–C$_8$alkyl denotes branched or unbranched alkyl such as methyl, ethyl, propyl, isopropyl, n-butyl, sec.butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, 2-ethylhexyl or n-octyl.

C$_1$–C$_8$alkoxy are straight-chain or branched residues such as methoxy, ethoxy, propoxy, butoxy, pentoxy, hexyloxy, heptyloxy or octyloxy.

Halogen denotes fluorine, bromine or, preferably, chlorine.

In the above reaction scheme, in formulae (6) and (7), preferably R is C$_1$–C$_4$alkyl, especially methyl.

For the first reaction step, there may be used, as chlorinating agent, e.g. sulfuryl chloride or, preferably, gaseous chlorine. The reaction is preferably conducted in the presence of a catalyst, such as dibenzothiophene, methyl sulfide, propyl sulfide, phenyl sulfide, a Lewis acid, such as aluminium chloride, or mixtures of these compounds. Especially suitable as catalyst for the chlorination reaction according to the invention is a mixture of propyl sulfide and an equimolar amount of aluminium chloride. For the reaction in the first step, the temperature can be selected from within a wide range, e.g. from −10 to 50° C. Preferably, the reaction is conducted at a temperature from 0 to 40° C. The reaction time can also vary within a wide range. Usually the reaction is conducted within a time span of 1 to 48, preferably 2.5 to 10 hours.

The acylation reaction (2. step) is usually conducted in the presence of a Lewis acid, e.g. aluminium chloride. The Lewis acid may be used in amounts of 1 to 3 molar, preferably 1.25 to 2 molar amounts, based on the chlorinated compound of formula (5). A suitable acylating reagent for use in this reaction is an acyl halide, preferably acetyl chloride. Further suitable acylating agents are e.g.

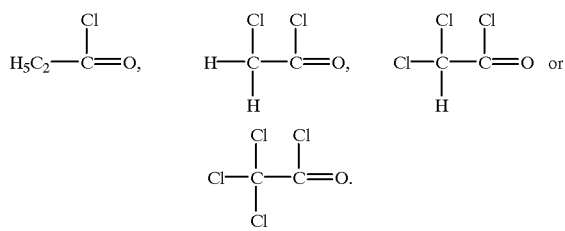

The Lewis acid and acylating reagents are preferably used in equimolar amounts. The reaction may be effected in solvents which are conventionally used for Friedel-crafts reactions, such as halogenated solvents like methylene chloride or ethylene chloride. The reaction time for this reaction step is of secondary importance and can be varied within a wide range, e.g. from 1 to 18 hours.

After the acylation reaction, the reaction mixture may optionally be subjected to a further chlorination reaction, in an analogous manner to the first reaction step, especially if, in the first reaction step, mixtures of differently chlorinated diphenyl compounds are obtained, such as mixtures of 4,4'-dichlorodiphenyl- and 2,4,4'-trichlorodiphenyl compounds. By the subsequent chlorination, uniformly chlorinated acyl compounds are produced.

The chlorination reaction (first step) and the acylation reaction (second step) and the optional further chlorination reaction are preferably conducted in the same reaction vessel, that is in one-pot reactions.

The oxidation of the acyl compound of formula (6) to give the compound of formula (7) (Baeyer-Villiger oxidation), may be effected with various oxidizing agents. Suitable oxidizing agents are, e.g.:

an equimolar mixture of dilute peracetic acid and acetic anhydride in the presence of a catalytic amount of perchloric acid;

an excess of 3-chloro-perbenzoic acid in water;

di-peroxydodecanedioic acid (DPDDA);

a mixture of dilute peracetic acid and acetic anhydride and sulfuric acid;

a mixture of m-chloroperbenzoic acid (MCPBA), trifluoroacetic acid and dichloromethane;

a mixture of sodium borate and trifluoroacetic acid;

a mixture of formic acid, hydrogen peroxide, acetic anhydride, phosphorus pentoxide and acetic acid;

a mixture of acetic acid, hydrogen peroxide, acetic anhydride and phosphorus pentoxide;

a mixture of $K_2S_2O_8$, sulfuric acid and a 1:1 water/methanol mixture;

a mixture of acetic acid and the potassium salt of monoperoxomaleic acid;

a mixture of trichloromethylene, the potassium salt of monoperoxomaleic acid and sodium hydrogen sulfate;

a mixture of maleic anhydride, acetic anhydride, hydrogen peroxide and trichloromethane;

a mixture of maleic anhydride, a urea-hydrogen peroxide complex and acetic acid; and Mg-mono-perphthalate.

Preferably there is used for the oxidation, a mixture of maleic anhydride, a urea-hydrogen peroxide complex and acetic acid as solvent.

If desired, a commercially available wetting agent may be added to the oxidizing agent.

The reaction times lie within a wide range and may vary from about 1 hour to about a week, from 4 to 6 days being preferred.

The reaction temperature ranges from −20° C. to about 80° C. Preferably, the reaction is conducted at room temperature.

The final hydrolysis to the desired halogeno-o-hydroxydiphenylethers of formula (1) proceeds quantitatively.

Preferably, the process according to the present invention relates to the production of halogeno-o-hydroxydiphenyl compounds having the formula (1) in which X is oxygen, and especially those compounds in which m is 2 and n is 1.

Especially preferred is the compound of formula

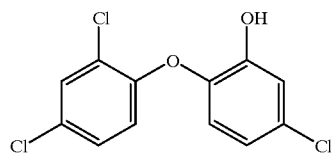

(3)

Some of the acyl compounds formed in the second reaction step (Friedel-Crafts acylation) are new compounds. These are the compounds having the formula

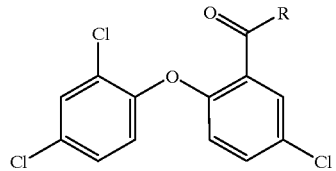

(8)

in which

R is unsubstituted $C_1$–$C_8$alkyl or $C_1$–$C_8$alkyl substituted by 1 to 3 halogen atoms or hydroxy; or unsubstituted $C_6$–$C_{12}$aryl or $C_6$–$C_{12}$aryl substituted by 1 to 3 halogen atoms, $C_1$–$C_5$alkyl or $C_1$–$C_8$alkoxy or combinations thereof.

In formula (8), preferably R is $C_1$–$C_4$alkyl, especially methyl.

These new compounds represent a further aspect of the present invention.

The halogeno-o-hydroxydiphenyl compounds produced according to the invention are insoluble in water but are soluble in dilute sodium- and potassium hydroxide solution and in practically all organic solvents. Due to these solubility properties, the application of the compounds in combatting microorganisms, especially bacteria, and in protecting organic materials against the attack by microorganisms is very versatile. Thus, they can be used, e.g. together with wetting- or dispersing agents, as soaps or synthetic detergent solutions for the disinfection and cleaning of human skin and hands, or they can be applied to these from solid articles in diluted or undiluted form.

The following Examples further illustrate the invention, but without limiting it.

EXAMPLE 1a

Chlorination of Diphenylether and Direct Use of the Reaction Product For Reaction With Acetyl Chloride Reaction scheme:

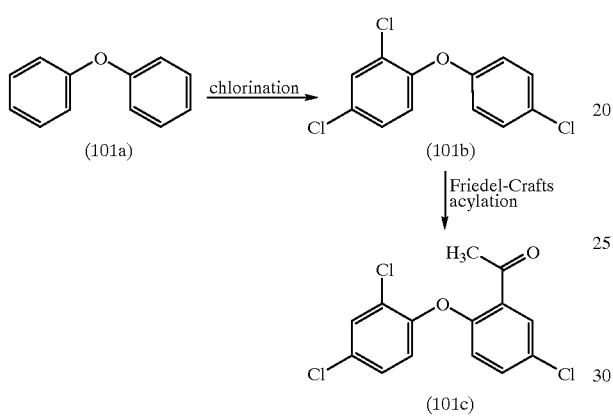

A mixture of 265 g (1.56 mol) of diphenylether (formula 101a), 7.36 g (0.06 mol) of dipropyl sulfide and 7.46 g (0.06 mol) of AlCl₃ are placed in a reaction vessel and melted by stirring and warming to 30° C. The chlorination is conducted by introducing gaseous chlorine at such a rate the reaction mixture can be held at a temperature below 40° C. by external cooling. The reaction is monitored using gas- or liquid chromatography. The chlorination is stopped when the content of 2,4,4'-trichlorodiphenylether (compound of the formula 101b) reaches 80 area % (about 6 hours introduction time).

For the acylation, 265 g (3.37 mol) of acetyl chloride are added, dropwise, on to 450 g (3.37 mol) of AlCl₃ in 1100 mls of 1,2-dichloroethane, at 20° to 40° C. The reaction mixture is stirred for 15 minutes at 40° C. Finally, the solution is added, dropwise, to the chlorination reaction mixture in 800 mls of dichloroethane at a temperature of 40° C. over about 1 hour. The reaction mixture is then stirred for 10 hours at about 400° C.

The reaction mixture is worked up by treating it with about 4 kg of ice and 550 mls of conc. HCl and extracting it for a short time. An aqueous phase and an organic phase are formed which are separated. After distilling off the solvent from the organic phase, there remains a dark, viscous residue which crystallizes on standing.

Yield: about 490 g of reaction mixture; content of main component about 340 g, corresponding to about 70% of theory, based on diphenylether (formula 101a) used.

Main component: 2-acetyl-4,2,4'-trichlorodiphenylether corresponding to formula (101c).

Composition of the reaction mixture (area % GC or LC): about 70% main component, about 15% 2,2',4,4'-tetrachlorodiphenylether with the rest being unknown compounds.

The reaction mixture can be used directly for the subsequent Baeyer-Villiger oxidation (Example 1b).

EXAMPLE 1b

Baeyer-Villiger Oxidation

Reaction scheme:

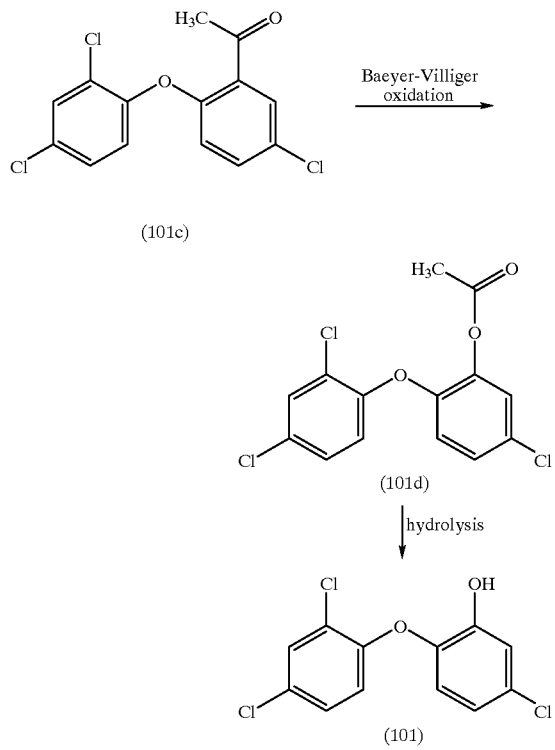

6.32 g of the 2-acetyl-4,2,4'-trichlorodiphenylether corresponding to formula (101c) produced in Example 1a) and 6.88 g of m-chloroperbenzoic acid (MCPBA) are dispersed with a wetting agent in 40 mls of water at 20 to 25° C. The suspension is heated to 80° C. and held at this temperature, with vigorous stirring, for 3 hours. 30 mls of tetrachloroethylene are added, whereupon two clear phases are formed. The excess peracid is decomposed by adding 0.5 g of sodium hydrogen sulfite, the mixture is adjusted to a pH value of about 8 with NaOH and the aqueous phase (containing m-chloroperbenzoic acid) is separated.

The phenolether of formula (101d) can be recovered, as a white powder of m.pt. 48–49° C., by crystallization from the organic phase For the hydrolysis, some water is added to the organic phase and the pH value is adjusted to 12 with sodium hydroxide. The end product of formula (101) is obtained from the intermediate product of formula (101d). The pH value is adjusted to about 1 with hydrochloric acid, the aqueous phase is separated and the tetrachloroethylene phase is concentrated.

5.7 g of a yellowish oil are obtained which contains about 80 area % of the compound of formula (101). After recrystallisation from petrol ether, the product is obtained as a white powder having a melting point of 55 to 56° C. The data agree with those of the original compound.

EXAMPLE 1c

Alternative Baeyer-Villiger Oxidation in Anhydrous Medium

To a solution of 3 g (10 mmol) of 2-acetyl-4,2,4'-trichlorodiphenylether corresponding to formula (101c) in 20 mls of anhydrous dichloromethane, there are added 4.5 g (13 mmol) of m-chloroperbenzoic acid. The mixture is cooled to 0° C. and 0.77 ml (10 mmol) of trifluoroacetic acid is added. The reaction mixture is allowed to slowly warm to room temperature. After a reaction time of 8 hours at room temperature, the reaction mixture is cooled with a sodium sulfite solution and washed with a saturated sodium bicarbonate solution. The dichloromethane layer is washed several times with water, dried over anhydrous sodium sulfate and concentrated until an oily residue is obtained. This residue is hydrolyzed by boiling it for 15 hours, under reflux, in 10 mls of 1N NaOH solution. There are obtained 2 g of a crude reaction product which, after acidification, is purified by column chromatography. In this way, there are formed 1.5 g (54% theory) of the compound of formula (101), as a white crystalline powder.

Alternative hydrolysis 0.9 g of the crude product obtained from the Baeyer-Villiger oxidation is boiled, for 4 hours under reflux, in 5 mls of ethanol which contains a few drops of concentrated HCl. The reaction is monitored by thin layer chromatography. After completion of the reaction, the alcohol is distilled off under vacuum. The oily residue is dissolved in 10 mls of dichloroethane and the solution is repeatedly washed with water. The organic phase is dried over anhydrous $Na_2SO_4$ and concentrated. There is formed 0.8 g of the crude compound of formula (101). By recrystallisation from petrol ether, there is obtained 0.64 g (70% theory) as a crystalline powder.

EXAMPLE 2

The procedure of Example 1a) is repeated except that the chlorination is conducted in an about 30% solution of diphenylether in 1,2-dichloroethane.

EXAMPLES 3 TO 6

For the acylation reaction described in Example 1a), in addition to acetyl chloride, the acylating agents set out in the following Table 1 can also be used:

TABLE 1

| Example | Acylating agent | Acylation product |
|---|---|---|
| 3 | | |
| 4 | | |

TABLE 1-continued

| Example | Acylating agent | Acylation product |
|---|---|---|
| 5 | | |
| 6 | | |

EXAMPLE 7

Acylation of a mixture of 2-acetyl-4,2,4'-trichlorodiphenylether and 4,4'-dichlorodiihenylether and a further chlorination reaction

EXAMPLE 7a

Acylation

Reaction scheme:

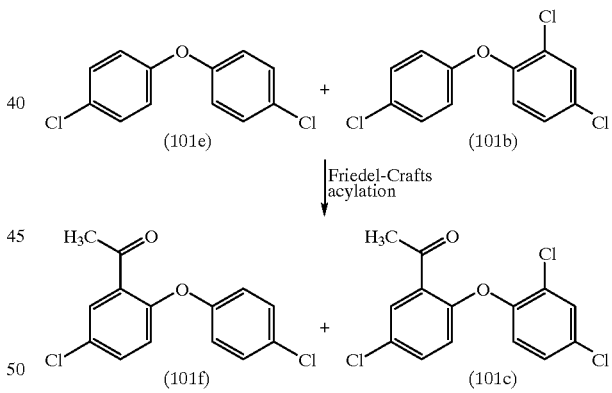

Into a three-necked sulfonation vessel equipped with a pressure-balanced dropping funnel, a nitrogen gas inlet tube, a stirrer and a safety tube, there are placed 480 mls of anhydrous 1,2-dichloroethane and 221.8 g (11.456 mol) of 88% aluminium chloride. The mixture is stirred and cooled in an ice bath under an atmosphere of nitrogen. To this mixture there are added 104 mls of freshly distilled acetyl chloride (114.4 g, 1.456 mol) over a period of 15 to 20 minutes. The exothermic reaction is allowed to cool to room temperature and the mixture is stirred for 30 minutes. A homogeneous dark brown mixture is formed, to which there is added, dropwise, with stirring at room temperature over 15 to 30 minutes, 251.9 g of a mixture containing 2,4,4'-trichlorodiphenylether (79%) (=compound of the formula (101b)) and 4,4'-dichlorodiphenylether (9%) (compound of formula (101b)), dissolved in 480 mls of anhydrous 1,2dichloroethane. The reaction is monitored by gas chromatography. After stirring for about 15 hours at room temperature, the mixture is added to 500 mls of ice water containing 50 mls of concentrated HCl. After stirring for 15 minutes, the organic phase is separated from the aqueous phase. The aqueous phase is extracted twice with 1,2-dichloroethane, using 100 mls of 1,2-dichloroethane each time. The combined organic phases are washed 6 times with water using 500 mls of water each time and dried over anhydrous sodium sulfate. After removing the solvent, there are obtained 244 g of a mixture containing the compound of formula (101c) and the compound of formula (101f).

This reaction mixture is used for the subsequent chlorination reaction.

EXAMPLE 7b

Further Chlorination

Reaction scheme:

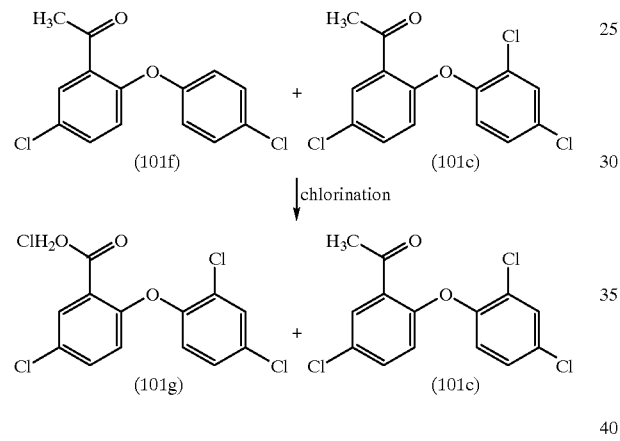

Into a sulfonation vessel equipped with a dropping funnel, a chlorine gas inlet tube, a stirrer, a safety tube and also a purification system for acidic vapors, there are placed 0.077 g (0.65 mmol) of propylsulfide and 88% aluminium chloride in 120 mls of anhydrous 1,2-dichloroethane. Chlorine gas is introduced into this mixture for 15 minutes with stirring. After interrupting the gas supply, there are added, dropwise over 1.5 to 2 hours, 244 g of a mixture conaining 2-acetyl-2,4,4'-trichlorodiphenylether (84.4%) and 2-acetyl-4,4'-dichlorodiphenylether (1.9%), dissolved in 120 mls of anhydrous 1,2-dichloroethane.

Chlorine gas is introduced, with stirring, for one hour. The reaction is monitored using gas chromatography. After completion of the reaction, the mixture is added to 500 mls of ice water containing about 15% HCl. The organic phase is separated and the aqueous phase is washed twice with 1,2-dichloroethane, using 100 mls of 1,2-dichloroethane each time. The combined organic phases are washed five times with a saturated sodium bicarbonate solution, using 200 mls of sodium bicarbonate solution each time, then washed five times with water, using 200 mls of water each time, and dried over sodium sulfate. Finally, the solvent is removed under vacuum. There are obtained 240 g of a crude product containing the compounds of formulae (101c) and (101g)

EXAMPLE 8

Acylation

Reaction scheme:

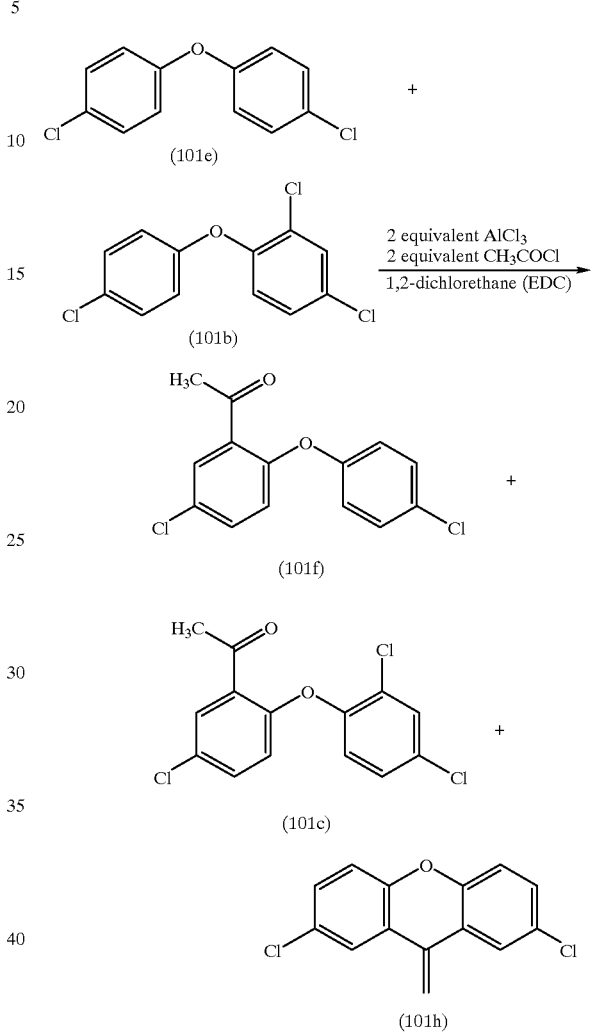

To a three-necked 500 ml round bottom flask equipped with a pressure equalizing dropping funnel, an overhead stirrer and a guard tube, 80 ml of 1,2-dichloroethane (EDC) and 9.85 g of $AlCl_3$ (0.0664 mol) are added under $N_2$-atmosphere. The mixture is cooled to 15° C. using a water bath, and under stirring 4.7 ml of acetyl chloride (5.18 g, 0.0660 mol) is added over a period of 30 to 45 minutes. To the above complex 10 g of a mixture of the compound of the formula (101e) (4,4'-dichlorodiphenylether, DCDPE), the compound of the formula (101b) (2,4,4'-trichlorodiphenylether, TCDPE) and 2,2',4,4'-tetrachlorodiphenylether (0.0333 mol w.r.t DCDPE and TCDPE together, TetCDPE) dissolved in 20 ml of EDC is added dropwise under stirring over a period of 20 minutes at room temperature. On addition of the chlorinating mixture no significant temperature increase is noted. The reaction starts refluxing and the reaction is monitored by GC (using FID and area normalization) at regular intervals. The reaction takes an hour for complete conversion of TCDPE to the compound of formula (101c). During the conversion, 2.3% of the compound of formula (101h) (=xanthene) is also formed.

The table below displays the course of reaction:

TABLE 2a

| Time | Conversion degree compound of formula | | | | |
|---|---|---|---|---|---|
| [min] | (101b) | (101e) + (101b) | (101f) | (101c) | (101h) |
| 30 | 3.0 | 9.6 | 7.8 | 73.5 | 2.0 |
| 60 | 1.0 | 8.9 | 7.2 | 75.0 | 2.3 |

In yet another reaction the amount of EDC is reduced form 10 volumes to 2 volumes and the reaction is done under identical conditions as above.

TABLE 2b

| Time | Conversion degree compound of formula | | | | |
|---|---|---|---|---|---|
| [min] | (101b) | (101e) + (101b) | (101f) | (101c) | (101h) |
| 30 | ≈0 | 9.3 | 4.5 | 75.1 | 3.5 |

EXAMPLE 9

Acylation

Reaction scheme:

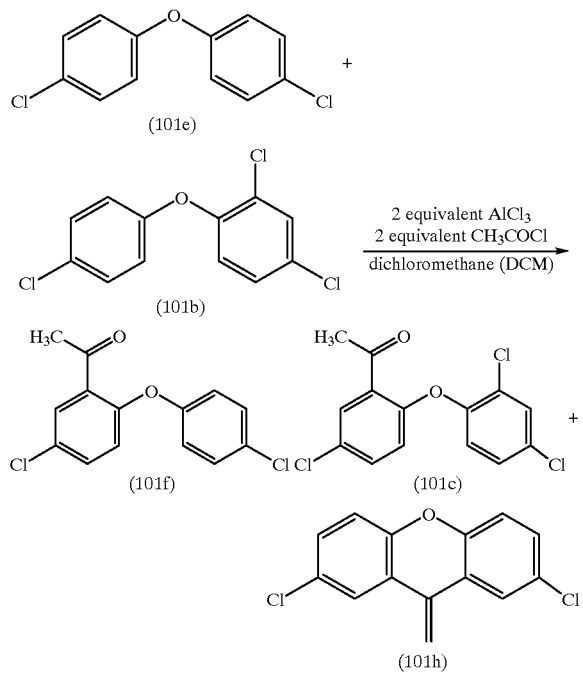

To a three-necked 20 l round bottom flask equipped with a pressure equalizing dropping funnel, an overhead stirrer and a guard tube, 7 l of dichloromethane (DCM) and 1088.2 g of $AlCl_3$ (7.328 mol) are added under $N_2$-atmosphere. The mixture is cooled to 15° C. using a water bath, and under stirring 522.9 ml of acetyl chloride (575.2 g, 7.328 mol) is added over a period of 20 minutes. During this time the internal temperature of the reaction is raised to about 20° C. The solution is stirred for 10 minutes more when the solution becomes clear. To the above complex 1100 g of a mixture of the compounds of the formulae (101e) (DCDPE), (101b) (TCDPE) and 2,2',4,4'-Tetrachlorodiphenylether (3.664 mol w.r.t DCDPE and TCDPE together) dissolved in 4000 ml of DCM is added under stirring over a period of 20 minutes with simultaneously heating the reaction mixture. On addition of the chlorinating mixture no significant temperature increase is noted. The reaction will reflux after nearly 1.5 hours. The sampling is done after a regular interval for estimating the extent of reaction on the basis of GC (using FID and area normalization). The reaction takes nearly 22–24 hours for conversion of TCDPE to the compound of formula (101c) (TCADPE). During the conversion, 1.3% of the compound of formula (101h) (xanthene) is also formed.

The GC data listed in table 3 show the conversion as a function of time:

TABLE 3

| Time | Conversion degree compound of formula | | | | | |
|---|---|---|---|---|---|---|
| [h] | (101e) | (101b) | (101e) + (101b) | (101f) | (101c) | (101h) |
| 2 | 3.7 | 64.0 | 10.3 | 6.8 | 13.9 | — |
| 6 | 0.5 | 35.4 | 10.2 | 9.6 | 42.9 | 0.3 |
| 11 | ≈0 | 10.6 | 9.9 | 10.0 | 67.3 | 0.7 |
| 16 | — | 1.1 | 9.3 | 9.3 | 75.3 | 1.0 |
| 22 | — | 0.2 | 9.0 | 8.7 | 76.6 | 1.3 |

EXAMPLE 10

Baeyer-Villiger oxidation

Reaction scheme:

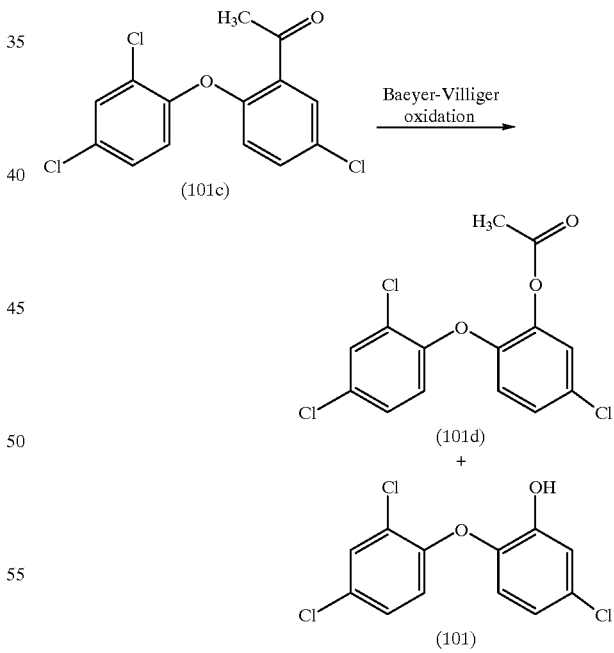

5 ml of acetonitrile is placed in a 50 ml round bottom flask and 0.75 g (0.0079 mol) of urea-hydrogenperoxide complex (UHP) and 92 mg (0.0008 mol) of maleic acid are added. To this stirred heterogeneous mixture 0.75 g (0.0076 mol) of maleic anhydride is added in portions at room temperature over 10 minutes. To the above solution 0.25 g (0.0008 mol) of the compound of formula (101c) is added. The reaction is continued further by stirring the reaction at room temperature. The reaction becomes clear after about 45 minutes and is monitored by GC (FID detector and area normalization). After 19 hours the reaction has proceeded to about 40% conversion.

The product distribution is found to be follows (Table 4):

TABLE 4

| GC taken after [h] | product distribution compound of formula | | |
|---|---|---|---|
| | (101c) | (101d) | (101) |
| 2 | 96.3 | 2.2 | 1.2 |
| 3.5 | 92.0 | 5.6 | 1.4 |
| 19 | 55.7 | 38.8 | 1.8 |

EXAMPLE 11

Baeyer-Villiger Oxidation (the reaction scheme is corresponding to Example 10)

25 ml of trifluoroacetic acid and 5 ml (0.0441 mol) of a 30% hydrogen peroxide solution is placed in a 100 ml round bottom flask. The mixture is stirred for 15 minutes and under stirring at room temperature 5.0 g (0.0158 mol) of the compound of formula (101c) is added. The reaction is continued further by stirring the reaction at room temperature. The solution turns yellowish orange after about 15 minutes and is monitored by GC analysis (FID detector and area normalization).

The product distribution is found to be as follows (Table 5):

TABLE 5

| GC taken after [h] | product distribution compound of formula | | |
|---|---|---|---|
| | (101c) | (101d) | (101) |
| 1 | 5.2 | 88.2 | 4.4 |
| 2 | 6.2 | 89.3 | 3.5 |
| 3 | 4.6 | 83.7 | 6.9 |
| 5 | 4.1 | 81.4 | 9.1 |
| 18.5 | 19.9 | 61.9 | 9.2 |

EXAMPLE 12

Baeyer-Villiger Oxidation (the reaction scheme is corresponding to Example 10)

15 ml of acetic acid is submitted in a two-necked 50 ml round bottom flask with a condenser and a dropping funnel. 4 ml (0.0280 mol) of a 70% solution of perchloric acid and 2.0 g (0.0063 mol) of the compound of formula (101c) is added. The homogeneous mixture is heated under stirring to 70–75° C. Using a dropping funnel 4.4 ml (0.0647 mol) of a 50% hydrogen peroxide solution is added dropwise over a period of 30 minutes. After completion the reaction is monitored by GC analysis (FID detector and area normalization).

The product distribution is found to be follows (Table 6):

TABLE 6

| GC taken after [h] | product distribution compound of formula | | |
|---|---|---|---|
| | (101c) | (101d) | (101) |
| 2 | 42.2 | 6.6 | 46.8 |
| 3.45 | 25.2 | 2.7 | 64.5 |
| 5.5 | 18.9 | 1.6 | 62.0 |
| 21 | 9.0 | 0.3 | 60.9 |

EXAMPLE 13

Baeyer-Villiger Oxidation (the Reaction scheme is corresponding to Example 10)

10 ml of water is submitted in a two-necked 100 ml round bottom flask with a dropping funnel. 10 ml of $H_2SO_4$ is added slowly. 2.0 g (0.0063 mol) of the compound of formula (101c) (2-acetyl-2',4,4'-trichloroacetyidiphenylether) is added and the 50% $H_2SO_4$ solution is heated to 80° C. The temperature is then further raised to about 130° C. To this solution 3.6 ml (0.318 mol) of 30% $H_2O_2$ is added dropwise over a period of about 15 to 20 minutes. After completion the reaction is monitored by GC analysis (FID detector and area normalization).

The product distribution is found to be follows (Table 7):

TABLE 7

| GC taken after [h] | product distribution compound of formula | | |
|---|---|---|---|
| | (101c) | (101d) | (101) |
| 2.5 | 39.2 | 13.6 | 30.3 |
| 19 | 24.6 | — | 54.2 |

What is claimed is:
1. A four step process for the production of a halogenated ortho-hydroxydiphenyl compound in which, in the first step, a diphenyl compound is chlorinated; in a second step the chlorinated compound is acylated in a Friedel-Crafts reaction and optionally again chlorinated after the acylation; in a third step the acyl compound is oxidized; and in a fourth step the oxidized compound is hydrolyzed; according to the following reaction scheme:

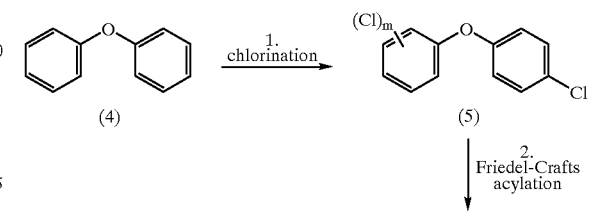

-continued

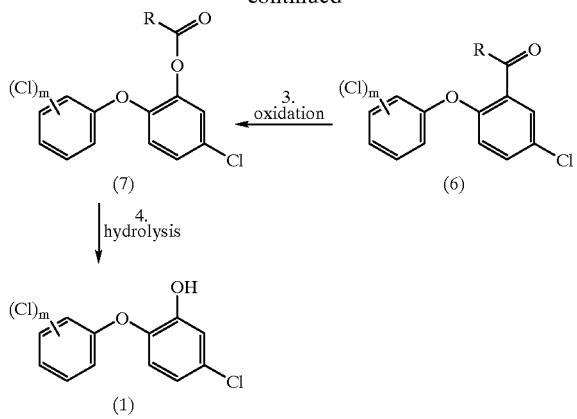

in which scheme:
R is unsubstituted $C_1$–$C_8$alkyl or $C_1$–$C_8$alkyl substituted by 1 to 3 halogen atoms or hydroxy; or unsubstituted $C_6$–$C_{12}$aryl or $C_6$–$C_{12}$aryl substituted by 1 to 3 halogen atoms, $C_1$–$C_5$alkyl or $C_1$–$C_8$alkoxy or a combination thereof; and
m is 1 to 3.

2. A process according to claim 1 wherein the first step chlorination is conducted with elemental chlorine.

3. A process according to claim 1 wherein the chlorination is conducted in the presence of a mixture of propyl sulfide and an equimolar amount of aluminium chloride.

4. A process according to claim 1 wherein a further chlorination follows after the acylation step.

5. A process according to claim 1 wherein the acylation reaction is conducted in the presence of acetyl chloride and aluminium chloride, whereby acetyl chloride and aluminium chloride are used in equimolar amounts.

6. A process according to claim 5 wherein the acylation reaction is conducted in the presence of a halogenated solvent.

7. A process according to claim 1 wherein the chlorination before the acylation reaction and the further optional chlorination are conducted as a one-pot reaction sequence.

8. A process according to claim 1 wherein the oxidation is conducted with a mixture of maleic anhydride, a urea-hydrogen peroxide complex and acetic acid as solvent.

9. A process according to claim 1 wherein in the formulas (6) and (7) R is $C_1$–$C_4$alkyl.

10. A process according to claim 9 wherein R is methyl.

11. A process according claim 1 wherein in formula (1) m is 2.

12. A compound having the formula

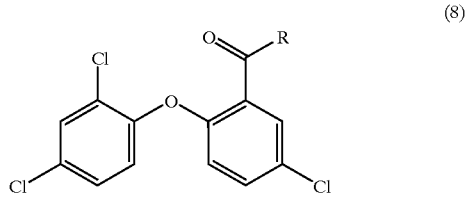

(8)

in which

R is unsubstituted $C_1$–$C_8$alkyl or $C_1$–$C_8$alkyl substituted by 1 to 3 halogen atoms or hydroxy; or unsubstituted $C_6$–$C_{12}$aryl or $C_6$–$C_{12}$aryl substituted by 1 to 3 halogen atoms, $C_1$–$C_5$alkyl or $C_1$–$C_8$alkoxy or combinations thereof.

13. A compound according to claim 12 in which R is $C_1$–$C_4$alkyl.

14. A compound according to claim 13 in which R is methyl.

* * * * *

UNITED STATES PATENT AND TRADEMARK OFFICE
CERTIFICATE OF CORRECTION

PATENT NO.    : 6,239,317 B1
DATED         : May 29, 2001
INVENTOR(S)   : Surendra Umesh Kulkarni et al.

It is certified that error appears in the above-identified patent and that said Letters Patent is hereby corrected as shown below:

<u>Title page,</u>
Item [30], should read:
-- Foreign Application Priority Data
[30] Jun. 25, 1997   (EP)              97810408 --.

Signed and Sealed this

Sixteenth Day of July, 2002

*Attest:*

*Attesting Officer*

JAMES E. ROGAN
*Director of the United States Patent and Trademark Office*